United States Patent [19]

Bennett

[11] 4,177,273
[45] Dec. 4, 1979

[54] 6-(SUBSTITUTED PHENYL)-4,5-DIHYDRO-PYRIDAZIN-3(2H)-ONES

[75] Inventor: Gregory B. Bennett, Mendham, N.J.

[73] Assignee: Sandoz, Inc., E. Hanover, N.J.

[21] Appl. No.: 915,549

[22] Filed: Jun. 14, 1978

Related U.S. Application Data

[63] Continuation-in-part of Ser. No. 768,558, Feb. 14, 1977, abandoned.

[51] Int. Cl.² ............... C07D 237/04; A61K 31/50
[52] U.S. Cl. ........................... 424/250; 544/239; 544/240
[58] Field of Search ............... 544/239, 240; 424/250

[56] References Cited

U.S. PATENT DOCUMENTS 3,317,530   2/1967   Reichenedir .................. 544/240

FOREIGN PATENT DOCUMENTS 41-06589   4/1966   Japan .................. 544/240

*Primary Examiner*—Mark L. Berch

*Attorney, Agent, or Firm*—Gerald D. Sharkin; Robert S. Honor; Thomas O. McGovern

[57] ABSTRACT

The present invention provides new pyridazinones of the formula

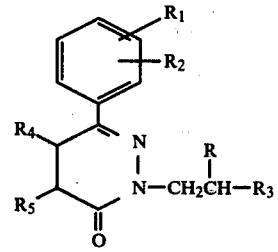

where
R is alkyl;
$R_1$ and $R_2$ are halo, alkyl, alkoxy, amino; nitro or trifluoromethyl;
$R_3$ is hydrogen, hydroxy, or acyloxy;
$R_4$ is hydrogen or alkyl; and
$R_5$ is hydroxy or acyl;

which are useful as central nervous system depressants.

14 Claims, No Drawings

6-(SUBSTITUTED PHENYL)-4,5-DIHYDRO-PYRIDAZIN-3(2H)-ONES

This is a continuation-in-part of Ser. No. 768,558, filed Feb. 14, 1977, abandoned.

This invention related to derivatives of 4,5-dihydro-4-hydroxy and 4-acyl-pyridazin-3(2H)-ones. More particularly, it relates to 2-alkyl, 2-hydroxyalkyl and 2-acyloxy substituted 4,5-dihydro-4-hydroxy and 4-acyl-pyridazin-3(2H)-ones, to methods for their preparation, and to their use in pharmaceutical compositions.

The compounds of this invention may be represented by the following formula:

where
- R is lower alkyl having 1 to 4 carbon atoms, i.e., methyl, ethyl, isopropyl, etc.;
- $R_1$ and $R_2$ each independently represent hydrogen, halo having an atomic weight of about 19 to 36, lower alkyl having 1 to 4 carbon atoms, e.g., methyl, ethyl, isopropyl and the like; lower alkoxy having 1 to 4 carbon atoms, e.g., methoxy ethoxy, isopropoxy, and the like; amino; nitro; or trifluoromethyl;
- $R_3$ is hydrogen, hydroxy or lower acyloxy having 2 to 5 carbon atoms, e.g., acetoxy, propionoxy, isobutyloxy, and the like;
- $R_4$ is hydrogen or lower alkyl of 1 to 4 carbon atoms; and
- $R_5$ is hydroxy or lower acyl having 2 to 5 carbon atoms, e.g., acetyl, propionyl, isobutyryl, and the like;

provided that (a) when both $R_1$ and $R_2$ represent trifluoromethyl or tertiary butyl, they are on other than adjacent carbon atoms; (b) that when $R_1$ is nitro, $R_2$ is hydrogen or nitro; (c) than when $R_3$ is is hydrogen, $R_5$ is hydroxy; and (d) that when $R_3$ is lower acyloxy, $R_5$ is lower acyl having the same number of carbon atoms as $R_3$.

The compounds of formula (I) where $R_5$ is hydroxy are prepared in accordance with the following process:

where
- $R_3'$ is hydrogen or hydroxy,
- $R_6$ is hydrogen or lower alkyl having 1 or 2 carbon atoms and
- R, $R_1$, $R_2$, $R_4$ and the provisos are as set out above.

The compounds of formula (Ia) are prepared by condensing a 2-hydroxy-γ-keto-butyric acid or ester (II) with a hydrazine of formula (III). The reaction is preferably run in inert solvents, e.g., the lower alkanols of 1 to 4 carbon atoms such as methanol, ethanol, n-butanol and the like, and aromatic and chloro substituted aromatic hydrocarbons, especially toluene, xylene, chlorobenzene and dichlorobenzene. The condensation may be carried out by heating a mixture of a compound of formula (II) and a compound of formula (III) in an inert solvent at temperatures of from about 50° to 200° C., preferably from 80° to 140° C. for 6 to 36 hours, preferably 12 to 18 hours. It is also preferred that the reaction be run in an inert atmosphere, e.g., nitrogen, argon, helium, etc. Neither the particular solvent nor the temperature or time at which the reaction is carried out is critical. The final product is recovered by conventional techniques, e.g., filtration and recrystallization.

The compounds of formula (I) in which $R_5$ is acyl and $R_3$ is acyloxy are prepared in accordance with the following process:

where
- X is chlorine or bromine,
- $R_5''$ is lower acyl having 2 to 5 carbon atoms, $R_7$ is dialkylamino having 2 to 8 carbon atoms, e.g., diethylamino, diisopropylamino, and the like, and R, $R_1$, $R_2$, $R_4$ and the provisos are as set out above.

The compounds of formula (Ib) are prepared by treating a compound of formula (IV) with dialkylamino lithium of formula (V) followed by alkylation with an acyl halide of formula (VI). The reaction between compound (IV) and compound (V) is preferably carried out in an inert solvent, e.g., aliphatic hydrocarbons such as pentane or hexane or aliphatic ethers such as diethyl ether or tetrahydrofuran, tetrahydrofuran being especially preferred, at temperatures of from $-70°$ to $40°$ C., preferably from $-20°$ to $20°$ C. for 1 to 18 hours, preferably from 8 to 12 hours. It is also preferred that the reaction be run in an inert atmosphere, e.g., nitrogen, argon, helium, etc. The compound of formula (VI) is added under the same reaction conditions and allowed to react for about 1 to 4 hours. The compound of formula (Ib) is recovered by standard techniques, e.g., extraction and distillation.

Many of the compounds of formulas (II), (III), (IV), (V) and (VI) are known and can be prepared by methods described in the literature. The compounds of formulas (II), (III), (IV), (V) and (VI) not specifically disclosed can be prepared from known starting materials by methods analogous to those described in the literature.

The compounds of formula (I) can occur as diastereo isomers, which can be separated by conventional means; and these isomeric forms are included in this invention.

The compounds of formula (I) are useful because they possess pharmacological activity in animals. In particular, the compounds of formula I in which $R_3$ and $R_5$ are hydroxy and $R_4$ is hydrogen are useful as central nervous system depressants, especially as minor tranquilizers and anti-convulsants, as indicated (1) by their ability to produce docility in behavior tests in mice given 25 to 200 milligrams per kilogram of animal body weight, i.p. of the test compound according to the 30-word adjective check sheet system basically as described by Irwin, S. (Gordon Research Conference, Medicinal Chemistry 1959) and Chen (Symposium on Sedative and Hypnotic Drugs, Williams and Wilkins, 1954); (2) by the method of Orloff, et al. (Proc. Soc. Exp. Biol., 70:254, 1949) using mice given 25 to 200 milligrams per kilogram of animal body weight, i.p. of the test compound after convulsive seizures are chemically induced with strychnine and metrazol; (3) by the convulsive seizure antagonism procedure in which 25 to 200 milligrams per kilogram of animal body weight of the test compound is administered intraperitoneally to 20 mice followed 1 hour later by 50 milligrams per kilogram of animal body weight, i.p. of N-sulfamoylazepine, a compound which causes a convulsant sequence including tonic convulsons and death simlar to those seen with pentylenetetrazol; (4) by the hexobarbital reinduction method of Winter (J. Pharmacol & Exp. Therap., 97:7, 1948) in which reinduction of anesthesia after recovery from hexobarbitol induced anesthesia is used to determine sedative hypnotic activity in mice given 70 milligrams per kilogram of animal body weight, i.p. of hexobarbital followed immediately after the mice regain their fighting reflexes by 25 to 200 milligrams per kilogram of animal body weight, i.p. of the test compound; and (5) by their activity in the rotorod test as described by Durham and Miya (J. Am. Pham. Assoc., 45, 208, 1957) in mice given 25 to 200 milligrams per kilogram of animal body weight of the test compound.

All of the compounds of formula (I) are useful as muscle relaxants as indicated by their ability to depress muscle twitches produced by peroneal nerve stimulation using a Grass 7 polygraph and S4 Grass stimulator and force displacement transducers sutured to the right tibialis anticus tendon in male cats given 0.3 to 30 milligrams per kilogram of animal body weight, i.v., of the test compound.

When the compounds are employed for the above utilities, they may be combined with one or more pharmaceutically acceptable carriers or adjuvants, and may be administered orally in such forms as tablets, capsules, elixirs, suspensions and the like, parenterally in the form of an injectable solution or suspension or in special forms such as suppositories and the like.

Depending upon the compound employed and the mode of administration, the exact dosage utilized may vary. However, in general, satisfactory results are obtained when the compounds are administered for the above uses at a daily dosage of from about 1 milligram to 200 milligrams per kilogram of animal body weight. This daily dosage is preferably given in divided doses, e.g., 2 to 4 times a day, or in sustained release form. For most large mammals, the total daily dosage is from about 75 to 2000 milligrams; preferably 75 to 500 milligrams; and dosage forms suitable for internal administration comprise from about 19 milligrams to about 1000 milligrams, preferably 19 to 250 milligrams of the compound in admixture with a solid or liquid pharmaceutical carrier or diluent.

The preferred compounds of formula (I) are those in which R is ethyl and $R_2$ is hydrogen and $R_1$, $R_3$, $R_4$ and $R_5$ are (a) H, OH, H and OH; (b) H, OH, Me, and OH; (c) H, H, Me and OH; and (d) p-Cl, OAc, H and Ac. These compounds are effective as muscle stimulants at a dose of 50 milligrams administered 2 to 4 times a day.

Tablets and capsules containing the ingredients indicated below may be prepared by conventional techniques and are useful as muscle relaxants and in treating tension and anxiety at a dose of one tablet or capsule 2 to 4 times a day.

| Ingredients | Weight (mg) tablet | capsule |
|---|---|---|
| 4,5-dihydro-4-hydroxy-2-(2-hydroxy-butyl)-6-phenyl-pyridazin-3(2H)-one | 50 | 50 |
| tragacanth | 10 | — |
| lactose | 197.5 | 250 |
| corn starch | 25 | |
| talcum | 15 | |
| magnesium stearate | 2.5 | |
| Total | 300 mg. | 300 mg. |

EXAMPLE 1

4,5-dihydro-4-hydroxy-2-(2-hydroxybutyl)-6-phenyl-pyridazin-3(2H)-one

A mixture of 3.5 grams (18 mmol) of 3-benzoyl-2-hydroxy-propionic acid and 1.9 grams (18 mmol) of 1-hydrazino-2-butanol in 40 ml of n-butanol is refluxed under nitrogen at 120° C. for 18 hours. After evaporation of the solvent, the product is partitioned between ether and water. The ether layer is washed with aqueous sodium bicarbonate and brine, dried over magnesium sulfate, and evaporated. The resulting residue is dissolved in 2% ethanol-chloroform and filtered through 200 grams of silica gel yielding after evaporation 4,5-dihydro-4-hydroxy-2-(2-hydroxybutyl)-6-phenylpyridazin-3(2H)-one, m.p. 92°–94° C.

The 4,5-dihydro-4-hydroxy-2-(2-hydroxybutyl)-5-phenylpyridazin-3(2H)-one of this example is useful as a minor tranquilizer and muscle relaxant when administered at a dose of 50 milligrams 2 to 4 times a day.

Following the above procedure, but using an equivalent amount of 3-(p-fluorobenzoyl)-2-hydroxy-propionic acid; 3-(p-chlorobenzoyl)-2-hydroxy-propionic acid; 3-(3,4-dichlorobenzoyl)-2-hydroxy-propionic acid; 3-(p-toloyl)-2-hydroxy propionic acid; 3-(p-methoxybenzoyl)-2-hydroxypropionic acid; 3-(p-aminobenzoyl)-2-hydroxy-propionic acid; 3-(3,5-dinitrobenzoyl)-2-hydroxy-propionic acid; 3-(m-trifluoromethylbenzoyl)-2-hydroxy-propionic acid or 3-benzoyl-2-hydroxy-3-methyl-propionic acid in place of the 3-benzoyl-2-hydroxy propionic acid, there is obtained 6-(p-fluorophenyl)-2-(2-hydroxybutyl)-4-hydroxy-4,5-dihydropyridazin-3(2H)-one; 6-(p-chlorophenyl)-2-(2-hydroxybutyl)-4-hydroxy-4,5-dihydropyridazin-3(2H)-one; 6-(3,4-dichlorophenyl)-2-(2-hydroxybutyl-4-hydroxy-4,5-dihydropyridazin-3(2H)-one; 6-(p-tolyl)-2-(2-hydroxybutyl)-4-hydroxy-4,5-dihydropyridazin-3(2H)-one; 6-(p-methoxyphenyl)-2-(2-hydroxybutyl)-4-hydroxy-4,5-dihydropyridazin-3(2H)-one; 6-(4-aminophenyl)-2-(2-hydroxybutyl)-4-hydroxy-4,5-dihydropyridazin-3(2H)-one; 6-(3,5-dinitrophenyl)-2-(2-hydroxybutyl)-4-hydroxy-4,5-dihydropyridazin-3(2H)-one; 6-(3-trifluoromethylphenyl)-2-(2-hydroxybutyl)-4-hydroxy-4,5-dihydropyridazine-3(2H)-one; or 4,5-dihydro-4-hydroxy-2-(2-hydroxybutyl)-5-methyl-6-phenylpyridazine-3(2H)-one (m.p. 137°–142° C.), respectively.

When the above procedure is carried out using equivalent amounts of 3-benzoyl-2-hydroxy-propionic acid and 1-hydrazino-2-hexanol or 3-benzoyl-2-hydroxy-propionic acid and 1-hydrazino-2-propanol or 3-benzoyl-2-hydroxy-3-methyl-propionic acid and butyl hydrazine in place of the 3-benzoyl-2-hydroxy-propionic acid and 1-hydrazino-2-butanol used therein, there is obtained 6-phenyl-2-(2-hydroxyhexyl)-4-hydroxy-4,5-dihydropyridazine-3(2H)-one; 6-phenyl-2-(2-hydroxypropyl)-4-hydroxy-4,5-dihydropyridazin-3(2H)-one; or 2-butyl-4,5-dihydro-4-hydroxy-5-methyl-6-phenyl-pyridazin-3(2H)-one (m.p. 129°–155° C.), respectively.

EXAMPLE 2

4,5-dihydro-2-(2-acetoxybutyl)-4-acetyl-6-(p-chlorophenyl)pyridazin-3(2H)-one

To a solution of 4.04 grams (40 mmol) of diisopropyl amine in 100 milliliters of anhydrous tetrahydrofuran at 0° C. is added 27 milliliters of a 1.5 N hexane solution of n-butyllithium (40 mmol) and the mixture is stirred for an hour at 0° C. A solution of 5.6 grams (20 mmol) of 4,5-dihydro-2-(2-hydroxybutyl)-6-(p-chlorophenyl)-pyridazin-3(2H)-one in 50 milliliters of anhydrous tetrahydrofuran is added dropwise and the resulting mixture is stirred at 0° C. under nitrogen for 18 hours. To this solution is added 5.0 milliliters (70 mmol) of acetyl chloride and, after stirring for an addition hour at 0° C., the mixture is partitioned between ether and water. The ether layer is washed with aqueous sodium bicarbonate and brine, dried over magnesium sulfate and evaporated to give on distillation at 150°–60°/0.1 mm., 4,5-dihydro-2-(2-acetoxybutyl)-4-acetyl-6-(p-chlorophenyl)-pyridazin-3(2H)-one as a light yellow oil.

What is claimed is:

1. A compound of the formula

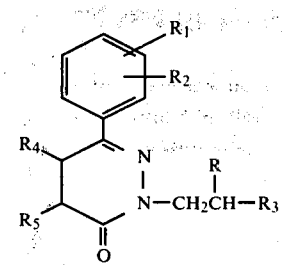

where
R is lower alkyl having 1 to 4 carbon atoms and
R$_1$ and R$_2$ each independently represent hydrogen, fluorine, chlorine, lower alkyl having 1 to 4 carbon atoms, lower alkoxy having 1 to 4 carbon atoms, amino, nitro or trifluoromethyl,
R$_3$ is hydrogen, hydroxy or lower alkanoyloxy having 2 to 5 carbon atoms,
R$_4$ is hydrogen or lower alkyl having 1 to 4 carbon atoms; and
R$_5$ is hydroxy or lower alkanoyl having 2 to 5 carbon atoms, provided (a) that when both R$_1$ and R$_2$ represent trifluoromethyl or tert-butyl they are on other than adjacent carbon atoms; (b) that when R$_1$ is nitro, R$_2$ is hydrogen or nitro; (c) that when R$_3$ is hydrogen, R$_5$ is hydroxy; and (d) that when R$_3$ is alkanoyloxy, R$_5$ is lower alkanoyl having the same number of carbon atoms as R$_3$.

2. A compound according to claim 1 in which R is ethyl.

3. A compound according to claim 1 having the formula

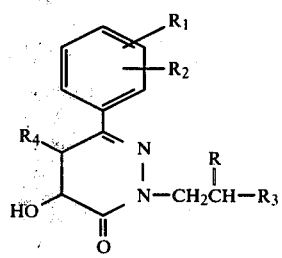

where R, R$_1$, R$_2$, R$_3$, R$_4$ and the proviso is as set out in claim 1.

4. A compound according to claim 3 in which R$_4$ is hydrogen.

5. A compound according to claim 4 in which R$_3$ is hydroxy.

6. A compound according to claim 3 in which R$_3$ is hydrogen.

7. A compound according to claim 1 in which R$_4$ is hydrogen and R$_3$ is alkanoyloxy having 2 to 5 carbon atoms and R$_5$ is alkanoyl having the same number of carbon atoms as R$_3$.

8. The compound of claim 1 which is 4,5-dihydro-4-hydroxy-2-(2-hydroxybutyl)-6-phenylpyridazin-3(2H)-one.

9. The compound of claim 1 which is 4,5-dihydro-4-hydroxy-2-(2-hydroxybutyl)-5-methyl-6-phenylpyridazin-3(2H)-one.

10. The compound of claim 1 which is 2-butyl-4,5-dihydro-4-hydroxy-5-methyl-6-phenylpyridazin-3(2H)-one.

11. The compound of claim 1 which is 4,5-dihydro-2-(2-acetoxybutyl)-4-acetyl-6-(p-chlorophenyl)-pyridazin-3(2H)-one.

12. A pharmaceutical composition useful as a minor tranquilizer, anti-convulsant, and muscle relaxant comprising a minor tranquilizer, anti-convulsant, and muscle relaxant effective amount of a compound according to claim 1 and a pharmaceutically acceptable carrier therefore.

13. A method of treating anxiety and tension which comprises administering to a mammal in need of said treatment a therapeutically effective amount of a composition according to claim 12 in which $R_3$ and $R_5$ are hydroxy and $R_4$ is hydrogen.

14. A method of treating muscle tension which comprises administering to a mammal in need of said treatment a therapeutically effective amount of a composition according to claim 12.

* * * * *